(12) United States Patent
Miyake et al.

(10) Patent No.: US 8,779,195 B2
(45) Date of Patent: Jul. 15, 2014

(54) POLYAMINE DERIVATIVES

(75) Inventors: Muneharu Miyake, Tokyo (JP); Tadashi Kusama, Tokyo (JP); Takashi Masuko, Tokyo (JP)

(73) Assignee: Nihon University, Tokyo (JP)

( * ) Notice: Subject to any disclaimer, the term of this patent is extended or adjusted under 35 U.S.C. 154(b) by 1461 days.

(21) Appl. No.: 12/514,540

(22) PCT Filed: Nov. 12, 2007

(86) PCT No.: PCT/JP2007/071937
§ 371 (c)(1),
(2), (4) Date: Jul. 28, 2009

(87) PCT Pub. No.: WO2008/059800
PCT Pub. Date: May 22, 2008

(65) Prior Publication Data
US 2010/0063322 A1    Mar. 11, 2010

(30) Foreign Application Priority Data

Nov. 15, 2006 (JP) .................. 2006-309325
Dec. 4, 2006 (JP) .................. 2006-327213

(51) Int. Cl.
C07C 303/00 (2006.01)
C07C 307/00 (2006.01)
C07C 309/00 (2006.01)
C07C 311/00 (2006.01)

(52) U.S. Cl.
USPC ....................................... 564/94

(58) Field of Classification Search
CPC ............... C07C 311/05; C07C 311/18
USPC ........................................ 564/94, 98
See application file for complete search history.

(56) References Cited

U.S. PATENT DOCUMENTS 6,646,149 B1 * 11/2003 Vermeulin et al. ............. 560/25

FOREIGN PATENT DOCUMENTS

EP        1 085 011 A1    3/2001
WO       WO 99/03823      1/1999

OTHER PUBLICATIONS

Veznik, F. et al., *Synthese von N¹, 4Di(p-cumaroyl)spermin, Einem Möglichen Biogenese-Vorläufer von Aphelandrin*, Helvetica Chimica Acta, vol. 74, No. 3, May 2, 1991, pp. 654-661.
Araneda, R. C. et al., *Effects of Polyamines on NMDA-Induced Currents in Rat Hippocampal Neurons: A Whole-Cell and Single-Channel Study*, Neuroscience Letters, vol. 152, 1993, pp. 107-112.
Benveniste, H. et al., *Elevation of the Extracellular Concentrations of Glutamate and Aspartate in Rat Hippocampus During Transient Cerebral Ischemia Monitored by Intracerebral Microdialysis*, vol. 43, No. 5, 1984, pp. 1369-1374.
Benveniste, M. et al.. *Multiple Effects of Spermine on N-Methyl-D-Aspartic Acid Receptor Responses of Rat Cultured Hippocampal Neurones*, Journal of Physiology, vol. 464, 1993, pp. 131-163.
Chao, J. et al., *N¹-Dansyl-Spermine and N¹-(n-Octanesulfonyl)-Spermine, Novel Glutamate Receptor Antagonists: Block and Permeation of N-Methyl -D-Aspartate Receptors*, Molecular Pharmacology, vol. 51, 1997, pp. 861-871.
Masuko, T. et al.. *A Regulatory Domain (R1-R2) in the Amino Terminus of the N-Methyl-D-Aspartate Receptor: Effects of Spermine, Protons, and Ifenprodil, and Structural Similarity to Bacterial Leucine/Isoleucine/Valine Binding Protein*, Molecular Pharmacology, vol. 55, 1999, pp. 957-969.
Masuko, T. et al., *Design and Synthesis of Novel Water-Soluble NMDA Receptor Antagonist with a 1,4,7,10-Tetraazacyclododecane Group*, Chem. Pharm. Bull, vol. 53, No. 4, 2005, pp. 444-447.
Masuko, T. et al., *Memantine: A Therapeutic Drug for Alzheimer's Disease and the Comparison with MK-801*, Nippon Yakurigaku Zasshi, vol. 124, 2004, pp. 145-151.
Masuko, T. et al., *Monoamines Directly Inhibit N-Methyl-D-Aspartate Receptors Expressed in Xenopus Oocytes in a Voltage-Dependent Manner*, Neuroscience Letters 371, 2004, pp. 30-33.
Parsons, C. G. et al., *Memantine is a Clinically Well Tolerated N-Methyl-D-Aspartate (NMDA) Receptor Antagonist—A Review of Preclinical Data*, Neuropharmacology, vol. 38, 1999, pp. 735-767.
Rock, D. M. et al., *The Polyamine Spermine has Multiple Actions on N-Methyl-D-Aspartate Receptor Single Channel Currents in Cultured Cortical Neurons*, Molecular Pharmacology, vol. 41, 1991, pp. 83-88.
Sengupta, D. et al., *A Microgonotropen Pentaaza Pentabutylamine and its Interactions with DNA*, Bioorganic and Medicinal Chemistry, vol. 4, No. 6, 1996, pp. 803-813.
Williams, K., *Ifenprodil Discriminates Subtypes of the N-Methyl-D-Aspartate Receptor: Selectivity and Mechanisms at Recombinant Heteromeric Receptors*, Molecular Pharmacology, vol. 44, 1993, pp. 851-859.
Williams, K., *Mechanisms Influencing Stimulatory Effects of Spermine at Recombinant N-Methyl-D-Aspartate Receptors*, Molecular Pharmacology, vol. 46, 1994, pp. 161-168.
Williams, K. et al., *Sensitivity of the N-Methyl-D-Aspartate Receptor to Polyamines is Controlled by NR2 Subunits*, Molecular Pharmacology, vol. 45, 1994, pp. 803-809.

* cited by examiner

*Primary Examiner* — Brandon Fetterolf
*Assistant Examiner* — Blaine G Doletski
(74) *Attorney, Agent, or Firm* — Morgan, Lewis & Bockius LLP

(57) ABSTRACT

A compound having the general formula (I) or a pharmacologically acceptable salt thereof:

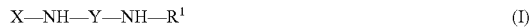

$$X—NH—Y—NH—R^1 \quad (I)$$

[wherein
X represents $R^2—SO_2—$ in which $R^2$ represents an optionally substituted lower alkyl group or phenyl group;
Y represents a group selected from the group consisting of $—R^3—NH—R^4—$, $—R^5—NH—R^6—NH—R^7—$, $—R^8—NH—R^9—NH—R^{10}—NH—R^{11}—$ and $—R^{12}—NH—R^{13}—NH—R^{14}—NH—R^{15}—$ in which $R^3$ to $R^{15}$ each independently represent a $C_3$ to $C_5$ alkylene group; and
$R^1$ represents hydrogen or an optionally substituted lower alkyl group, with the proviso that the case where X represents a tosyl group, Y represents $—(CH_2)_3—NH—(CH_2)_4—NH—(CH_2)_3—$ and $R^1$ represents hydrogen is excepted].

6 Claims, 5 Drawing Sheets

POLYAMINE DERIVATIVES

TECHNICAL FIELD

The present invention relates to novel polyamine derivatives having an N-methyl-D-aspartate (NMDA) receptor activity inhibitory effect.

BACKGROUND ART

Glutamate is a transmitter that manages excitatory neurotransmission in the brain and known as an excitatory amino acid. It has been reported that when the excitatory amino acid is extracellularly released in a large amount, abnormal excitation of the central nerve occurs and leads to various diseases such as the brain/spinal cord damage, Alzheimer's disease, Parkinson's disease, amyotrophic lateral sclerosis and Huntington's chorea; neurodegeneration; mental disorders; and functional motility disorders.

NMDA receptor, one of the glutamate receptors, is a tetrameric or pentameric assembly of a membrane protein having 4 membrane regions with a channel serving as an ion channel formed at the center. Usually, the channel is blocked by a magnesium ion. However, it is known that when the receptor is activated, sodium ions and calcium ions flow into a cell.

The NMDA receptor is involved in e.g., memory, learning and nerve development of mammalian brains. On the other hand, if the receptor is excited excessively, a large amount of calcium flows into a nerve cell and causes irreversible nerve-cell death in the brain. As a result, disorders such as motility disturbance, sensory disturbance and abnormal behavior may occur.

As a substance having an antagonistic action against NMDA receptor activity and specifically suppressing the activity of the receptor, memantine (general name: memantine hydrochloride) is known and widely applied as a therapeutic drug for Alzheimer's disease in a clinical setting in Europe and the U.S.A. Memantine attenuates calcium permeability through NMDA receptor in response to excessive release of glutamate, thereby protecting the nerve cells.

Furthermore, it is known that a kind of polyamine, spermine(N,N'-bis(3-aminopropyl)-1,4-diaminobutane) has a blockage action on NMDA receptor. However, the action of spermine on the NMDA receptor outside a cell strongly depends upon membrane potential. Spermine activates the receptor during depolarization (excitation) time and inhibits the activity of the receptor during hyperpolarization (resting) time (see, for example, Benveniste, M. et al. (Non-Patent Document 1), Rock, D. M. et al. (Non-Patent Document 2), Araneda, R. C. et al. (Non-Patent Document 3), Williams, K. et al. (Non-Patent Document 4) and Williams, K. (Non-Patent Document 5)). Because of such a two-track activity regulatory function, spermine is not suitably used as a medicinal drug.

Then, a spermine derivative has been proposed, which is designed by depriving it of the activity-promoting effect and maintaining and promoting only the inhibitory activity. As an example of the spermine derivative, $N^1$-Dansyl-Spermine (Dansyl-SPM) represented by the formula (III) below may be mentioned (for example, Chao, J. et al. (see Non-Patent Document 6)).

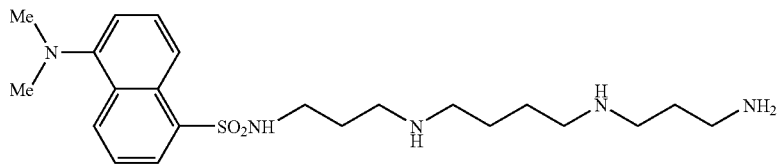

(III)

In Dansyl-SPM, a dansyl group is bonded to a nitrogen atom at an end of spermine to produce sulfone amide, which suppresses the activity-promoting effect on NMDA receptor and enhances only the activity inhibitory effect. Dansyl-SPM exhibits higher affinity for NMDA receptor than memantine.

On the other hand, use of a polyamine derivative as a medicinal drug is suggested, for example, in the specification of European Patent Application Publication No. 1085011 (Patent Document 1), which discloses a polyamine derivative having an inhibitory action on polyamine transportation or a polyamine binding protein and suggests that a polyamine derivative may be used as an anticancer drug. Furthermore, as a spermine derivative, e.g., Dansyl-SPM mentioned above and $N^1$-Tosyl-Spermine (Tosyl-SPM) represented by the formula (IV) below are mentioned as examples.

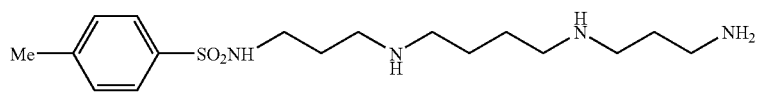

(IV)

Patent Document 1: European Patent Application Publication No. 1085011 (specification)

Non-Patent Document 1: Benveniste, M. et al., J, Physiol. (Lond.) 464: 131-163 (1993)

Non-Patent Document 2: Rock, D. M, et al., Mol, Pharmacol. 41: 83-88 (1992)

Non-Patent Document 3: Araneda, R. C. et al., Neurosci. Lett. 152: 107-112 (1993)

Non-Patent Document 4: Williams, K, et al., Mol. Pharmacol. 45: 803-809 (1994)

Non-Patent Document 5: Williams, K, Mol. Pharmacol. 46: 161-168 (1994)

Non-Patent Document 6: Chao, J. et al., Mol. Pharmacol. 51: 861-871 (1997)

DISCLOSURE OF THE INVENTION

Problems to be Solved by the Invention

However, Dansyl-SPM has a relatively strong cytotoxicity. Therefore, to apply it to a medicinal drug, a compound having higher affinity for NMDA receptor and low cytotoxicity is required.

On the other hand, one of the things that must be paid attention particularly in developing a brain-function protecting drug such as an Alzheimer's disease therapeutic drug, is transmigration of a developed compound into the brain. For a substance to transmigrate from the blood into the brain tissue, the substance must penetrate the blood brain barrier. However, substances except water, gas and lipid-soluble substances are limited in transmigrating from the blood into the brain tissue by the blood brain barrier. It is difficult to predict whether a compound penetrates the blood brain barrier or not, since it is determined by various properties of the compound. For example, it is known that the permeability is decreased if a compound has an excessively large molecular weight. Accordingly, it is required that a compound to be used as a brain function protecting drug does not have a large molecular weight or a complicated structure.

Then, it is an object of the present invention to provide a compound having sufficiently high affinity for NMDA receptor, efficiently inhibiting calcium ion inflow, having low cytotoxicity and a low molecular weight, thereby being expected to have good transmigration to the brain.

Means for Solving the Problems

The present inventors have conducted intensive studies with a view to attaining the aforementioned object. As a result, they found that a compound having affinity for NMDA receptor similar to Dansyl-SPM and having relatively week cytotoxicity can be obtained by binding a tosyl group to a polyamine. They further found that even if the same tosyl-group bound polyamine, cytotoxicity thereof can be remarkably reduced by employing, in the general formula (I) below, $(CH_2)_4$—NH—$(CH_2)_4$—NH—$(CH_2)_4$— as Y, or employing a guanidyl group as $R^1$. They finally found that a compound having sufficiently high affinity for NMDA receptor and significantly low cytotoxicity and further having a simple structure with a low molecular weight can be obtained by changing the tosyl group to a lower alkyl group. Based on the findings, the present invention was accomplished.

More specifically, the present invention relates to

[1] A compound having the general formula (I) or a pharmacologically acceptable salt thereof:

X—NH—Y—NH—$R^1$  (I)

[wherein X represents $R^2$—$SO_2$— in which $R^2$ represents an optionally substituted lower alkyl group or phenyl group; Y represents a group selected from the group consisting of —$R^3$—NH—$R^4$—, —$R^5$—NH—$R^6$—NH—$R^7$—, —$R^8$—NH—$R^9$—NH—$R^{10}$—NH—$R^{11}$— and —$R^{12}$—NH—$R^{13}$—NH—$R^{14}$—NH—$R^{15}$— in which $R^3$ to $R^{15}$ each independently represent a $C_3$ to $C_5$ alkylene group; and $R^1$ represents hydrogen or an optionally substituted lower alkyl group, with the proviso that the case wherein X represents a tosyl group and Y represents —$(CH_2)_3$—NH—$(CH_2)_4$—NH—$(CH_2)_3$— and $R^1$ represents hydrogen is excepted];

[2] The compound according to the above [1] or a pharmacologically acceptable salt thereof in which NH—$R^1$ represents a guanidyl group;

[3] The compound according to the above [1] or [2], or pharmacologically acceptable salt thereof, in which X represents a $C_4$ alkyl group or a tosyl group;

[4] A pharmaceutical composition comprising the compound according to any one of the above [1] to [3], or a pharmacologically acceptable salt thereof;

[5] An N-methyl-D-aspartate receptor activity inhibitor comprising a compound having the general formula (II) or a pharmacologically acceptable salt thereof

X—NH—Y—NH—$R^1$  (II)

[wherein X represents $R^2$—$SO_2$— in which $R^2$ represents an optionally substituted lower alkyl group or phenyl group; Y represents a group selected from the group consisting of —$R^3$—NH—$R^4$—, —$R^5$—NH—$R^6$—NH—$R^7$—, —$R^8$—NH—$R^9$—NH—$R^{10}$—NH—$R^{11}$— and —$R^{12}$—NH—$R^{13}$—NH—$R^{14}$—NH—$R^{15}$— in which $R^3$ to $R^{15}$ each independently represent a $C_3$ to $C_5$ alkylene group; and $R^1$ represents hydrogen or an optionally substituted lower alkyl group]; and

[6] A prophylactic or therapeutic drug for Alzheimer's disease or Parkinson's disease, comprising a compound having the general formula (II) or a pharmacologically acceptable salt thereof:

X—NH—Y—NH—$R^1$  (II)

[wherein X represents $R^2$—$SO_2$— in which $R^2$ represents an optionally substituted lower alkyl group or phenyl group; Y represents a group selected from the group consisting of —$R^3$—NH—$R^4$—, —$R^5$—NH—$R^6$—NH—$R^7$—, —$R^8$—NH—$R^9$—NH—$R^{10}$—NH—$R^{11}$— and —$R^{12}$—NH—$R^{13}$—NH—$R^{14}$—NH—$R^{15}$— in which $R^3$ to $R^{15}$ each independently represent a $C_3$ to $C_5$ alkylene group; and $R^1$ represents hydrogen or an optionally substituted lower alkyl group].

Advantages of The Invention

The compounds according to the present invention or pharmacologically acceptable salts thereof have high affinity for NMDA receptor and weak toxicity. Furthermore, the molecular weight is low and thus good transmigration to the brain can be expected. Accordingly, the compounds prevents excessive calcium inflow into the brain cells and are useful for protecting the brain function, e.g., as therapeutic drugs of Alzheimer's disease and Parkinson's disease.

Furthermore, of the compounds according to the present invention, TsPDG, BsPDG and TsSPMG, are not sensitive to polyamine oxidase since the amino groups at both ends are protected. When spermine is administered to a living body, polyamine oxidase possibly decomposes spermine to produce acrolein, increasing cytotoxicity. However, TsPDG, BsPDG and TsSPMG are advantageous since there is no risk of producing acrolein.

BEST MODE FOR CARRYING OUT THE INVENTION

With respect to a compound represented by the formula (I) (hereinafter referred to as a "compound (I)"), the definition of each symbol used therein will be described, below.

The "hydrogen or an optionally substituted lower alkyl group" represented by $R^1$ or $R^2$ may include a straight or branched alkyl group having 1 to 6 carbon atoms. Examples thereof may include methyl, ethyl, propyl, isopropyl, butyl, isobutyl, sec-butyl, tert-butyl, pentyl and hexyl. Examples of a substituent may include a halogen atom, a nitro group, a cyano group, a hydroxy group, an amino group and a carboxy group.

Furthermore, $R^1$ represents preferably hydrogen or a lower alkyl group having 1 to 3 carbon atoms, and more preferably NH—$R^1$ represents a guanidyl group. $R^2$ represents preferably a straight alkyl group having 3 to 5 carbon atoms, and particularly preferably an n-butyl group.

The "optionally substituted phenyl group" represented by $R^2$ refers to a phenyl group having 1 to 5 substituents at substitutable positions. Examples of the substituent may include a halogen atom (e.g., fluorine, chlorine, bromine and iodine), a nitro group, a cyano group, an optionally substituted $C_{1-6}$ alkyl group (e.g., a methyl group and an ethyl group), an amino-$C_{1-6}$ alkyl group (e.g., an aminomethyl group), a hydroxy group, an optionally substituted alkoxyl group (e.g., a methoxy group, an ethoxy group and a propoxy group). Particularly preferably, $R^2$ represents a methylphenyl group. In this case, $X(R^2—SO_2—)$ represents a tosyl group.

In "the group selected from the group consisting of —$R^3$—NH—$R^4$—, —$R^5$—NH—$R^6$—NH—$R^7$—, —$R^8$—NH—$R^9$—NH—$R^{10}$—NH—$R^{11}$— and —$R^{12}$—NH—$R^{13}$—NH—$R^{14}$—NH—$R^{15}$—" represented by Y, $R^3$ to $R^{15}$ each independently represent a $C_3$ to $C_5$ alkylene group. Preferably $R^3$ to $R^{15}$ represents each an alkylene group having 3 or 4 carbon atoms.

However, a compound where X represents a tosyl group, Y represents —$(CH_2)_3$—NH—$(CH_2)_4$—NH—$(CH_2)_3$ and $R^1$ represents hydrogen, that is, a compound (Tosyl-SPM) having the general formula (IV) below, is excepted from the compounds (I), The salts of the compounds (I) are not particularly limited as long as they are pharmacologically acceptable salts. The salts there of may include salts with inorganic acids such as hydrochloric acid, sulfuric acid, carbonic acid, bicarbonic acid, hydrobromic acid and hydroiodic acid; salts with organic carboxylic acids such as acetic acid, maleic acid, lactic acid, tartaric acid and trifluoroacetic acid; salts with organic sulfonic acids such as methanesulfonic acid, hydroxy methanesulfonic acid, hydroxy ethane sulfonic acid, benzenesulfonic acid, toluenesulfonic acid and taurine acid; salts with amines such as trimethylamine, triethylamine, pyridine, procaine, picoline, dicyclohexylamine, triethanolamine, tris(hydroxymethylamino)methane, and phenethylbenzylamine; and salts with amino acids such as arginine, lysine, serine, glycine, aspartate and glutamate.

Compounds (I) according to the present invention may be hydrates, non-hydrates or other solvates.

Next, a method for producing a compound (I) will be specifically described.

A compound (I) can be produced, for example, by the method shown in the scheme below or in accordance with an equivalent method thereof.

First, a compound (I) where X represents a tosyl group and Y represents —$R^5$—NH—$R^6$—NH—$R^7$—, that is, a compound represented by the formula (IX) below, can be synthesized by the method represented by Scheme I using a compound represented by the formula (X) below as a starting substance (i).

Ts-NH—$(CH_2)n$-NH—$(CH_2)n$-NH—$(CH_2)n$-Cbz    (IX)

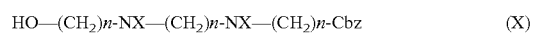
HO—$(CH_2)n$-NX—$(CH_2)n$-NX—$(CH_2)n$-Cbz    (X)

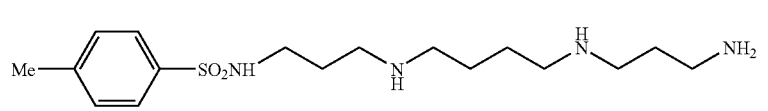

(IV)

Preferable examples of the compounds (I) may include TsSPMG, TsPD, TsPDG and BsPDG represented by the formula (V) to (VIII) below.

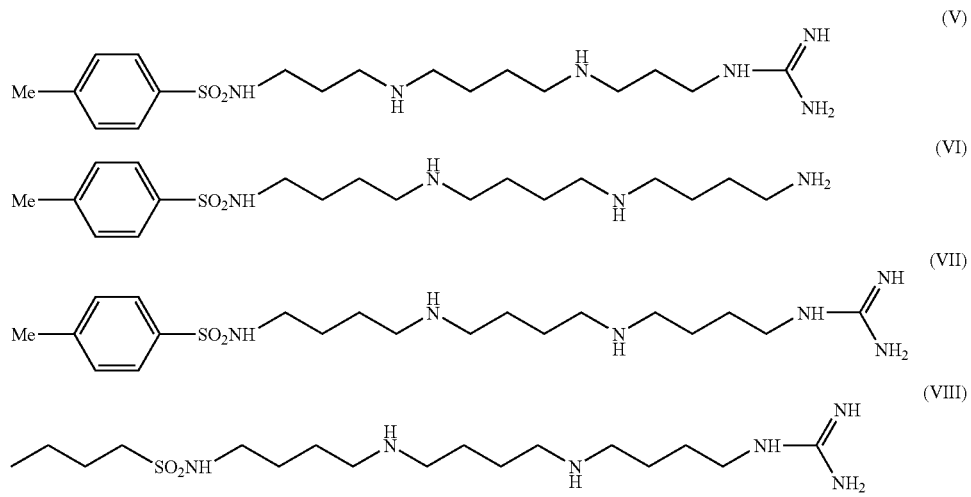

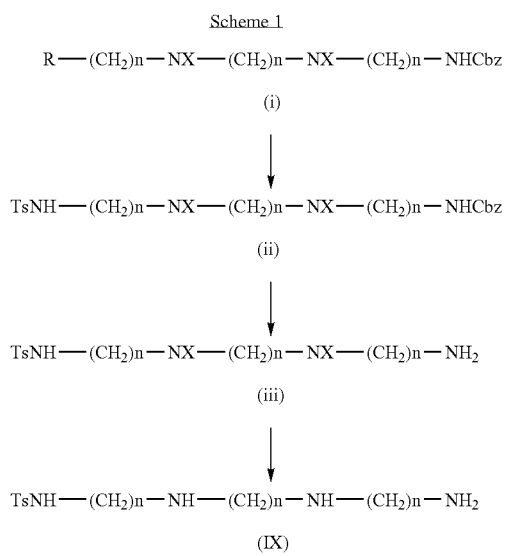

Scheme 1 wherein Ts represents a tosyl group; Cbz represents a benzyloxy carbonyl group; and X represents a protecting group for an amino group, for example, a tert-butoxycarbonyl group (Boc).

First, to a starting substance (i), methanesulfonyl chloride and triethylamine are added to react them. In this manner, R is substituted by an OMs group. The reaction is performed in $CH_2Cl_2$. After the reaction mixture is stirred at 0° C. for 2 hours, stirring is performed at room temperature overnight. The reaction mixture is washed with brine and the solvent is removed. Thereafter purification is performed by silica gel column chromatography, etc.

Subsequently, treatment with $NaN_3$ is performed to substitute the OMs group by an $N_3$ group. The reaction is performed in DMF while stirring at room temperature overnight. The mixture is diluted with ethyl acetate, etc., washed with water. After the solvent is evaporated, purification is performed by silica gel column chromatography, etc.

Then, to the compound thus obtained, a tosyl group is bonded to obtain a compound (ii). First, a compound (i) where R is $N_3$ is hydrogenated in a THF solution in the presence of a catalyst such as palladium carbon ethylenediamine complex. After the catalyst is removed and the solution is concentrated, p-toluenesulfonyl chloride (TsCl) is reacted with triethylamine. The reaction is performed while stirring at room temperature. About 18 hours later, the reaction mixture is diluted with $CH_2Cl_2$, washed with brine, and allowed to dry. Thereafter, purification is performed by silica gel column chromatography to obtain the compound (ii).

Subsequently, the NHCbz group of the compound (ii) is substituted by an amino group. First, the compound (ii) is hydrogenated in a THF solution. Hydrogenation is performed by placing the compound under an $H_2$ atmosphere at room temperature for 24 hours in the presence of e.g., palladium carbon, as a catalyst. Then, the catalyst is filtered off and purification is performed by silica gel column chromatography to obtain a compound (iii).

Finally, the protection group is removed to obtain a compound (iv). The deprotection method can be appropriately selected depending upon the type of protecting group. For example, in the case of Boc, the protecting group can be removed by adding concentrated hydrochloric acid to render the conditions highly acidic.

On the other hand, in the case of a compound (I) where $R^1$ is a guanidyl group, the guanidyl group is bonded to an amino group before deprotection. In this case, the compound (iii) is reacted with 1,3-bis(tert-butoxycarbonyl)-2-methyl-2-thiopseudourea in $CH_2Cl_2$. The reaction is performed at room temperature for 48 hours while stirring. After filtration, the reaction mixture is concentrated and purified by silica gel column chromatography, and thereafter deprotection is performed to obtain a desired compound.

Furthermore, in the case of a compound (I) where $R^2$ is a lower alkyl group, R of the compound (i), in the above scheme 1, is substituted by $N_3$ and hydrogenated to convert $N_3$ into an amino group. To the amino group, an $—R^2—SO_2—$ group can be bonded in accordance with a known method. For example, in the case where $R^2$ is a butyl group, butanesulfonyl chloride (BBCl) and triethylamine are added to a $CH_2Cl_2$ solution of a compound (i) and stirred at room temperature for 18 hours to react them. The mixture is diluted with $CH_2Cl_2$, washed, concentrated and purified by silica gel column chromatography.

After that, in accordance with the aforementioned method, the NHCbz group is converted into an amino group, a guanidyl group is added to the amino group, and then, a protecting group is removed to synthesize various compounds (I).

In the present invention, a starting substance (i) (where, e.g., Y represents $—(CH)_4—NH—(CH)_4—NH—(CH)_4—$) can be synthesized by the method of Sengupta et al. (D. Sengupta et al., Bioorganic and Medicinal Chemistry, 4 (6) 803-813 (1996)). Other compounds can be also synthesized by known methods.

The aforementioned compound (I) and Tosyl-SPM (compound IV) represented by the general formula (I) wherein X represents a tosyl group; Y represents $—(CH_2)_3—NH—(CH_2)_4—NH—(CH_2)_3—$, and $R^1$ represents hydrogen (hereinafter compounds (I) and (IV) are collectively referred to as "compound (II)") have an excellent NMDA receptor function suppression effect. This is because the compound (II) serves as an ion channel blocker.

For example, at the time of cerebral ischemia, it is known that a large amount of glutamate is extracellularly released (Benveniste, H. et al., J. Neuroche., 43, 1369 (1984)). The compound (II) can prevent inflow of a large amount of calcium ions into cells, even if NMDA receptor is abnormally activated by high-level glutamate. In this manner, the compound (II) can prevent necrosis of the nerve cells.

Furthermore, the compound (II) is effective for various types of diseases attributed to the NMDA receptor and useful also as a therapeutic, improving and prophylactic drugs for chronic neurodegenerative diseases such as Alzheimer's disease, Parkinson's disease, amyotrophic lateral sclerosis and Huntington's chorea; epilepsy; pains derived from chronic pain, migraine headache, cancer-related pain and diabetic neuropathy; spastic palsy; multiple sclerosis and encephalomyelitis.

The compound (II) may be used together with various drugs to be used in combination.

Examples of such drugs to be used in combination may include other NMDA antagonists; substances inhibiting the formation or function, or accelerating removal of toxic products (e.g., nitrogen oxide, reactive oxygen and a nitrogen intermediate; a lipid peroxide, an interleukin, a cytokine, a chemokine, a hydrogen ion) to be formed by cerebral ischemia; substances inhibiting depolarization of cells caused by cerebral ischemia or activating a signal path against depolarization; substances inhibiting the mechanism of apoptosis;

and substances inhibiting supplement of immune cells responsive to ischemia and inhibiting adhesion of immune cells to the blood vessel.

Examples of the "other NMDA antagonists" may include substances (e.g., D-2-amino-5-phosphonovaleric acid) antagonistically binding to a binding site of an agonist such as glutamate and NMDA; substances (e.g., 7-chlorokynurenic acid) antagonistically binding to a binding site of glycine required for activating the NMDA receptor by an agonist; substances (e.g., alkaine) antagonistically binding to a binding site of a polyamine serving as an activity enhancing agent; and other open-channel blockers (e.g., MK-801, $Mg^{2+}$).

Examples of the "substances inhibiting the formation or function, or accelerating removal of toxic products to be formed by cerebral ischemia" may include an antioxidation compound, a neutrophile inhibitor (NIF), a sodium channel antagonist, an NOS inhibitor, a potassium channel opening agent, a glycine-site antagonist, an AMPA/kainic acid acceptor antagonist, a calcium channel antagonist, a $GABA_A$ receptor modulator and an anti inflammatory agent.

Examples of the "substances inhibiting depolarization of cells caused by cerebral ischemia or activating a signal path against depolarization" may include substances activating a $GABA_A$ receptor, activating a voltage or ligand control potassium channel and activating a voltage or ligand control chlorine channel. More specifically, a potassium channel opening agent and a $GABA_A$ receptor agonist, etc. can be used.

Examples of the "substances inhibiting the mechanism of apoptosis" may include substances activating FAS/TNFα/p75 receptor, activating caspase, activating NFκB, JNK and/or p38 kinase signal cascade, inhibiting mitochondrial collapse, activating the mitochondrial permeability transition pore and activating protease between the cells such as calpain. More specifically, a caspase inhibitor, an inhibitor of an enzyme serving as a mediator for apoptosis mechanism, etc. can be used.

Examples of the "substances inhibiting supplement of immune cells responsive to ischemia" may include cytokines and chemokines. Examples of the "substances inhibiting adhesion of immune cells to the blood vessel" may include antagonists against cytokine and chemokine receptors and antibodies against NIF and cell adhesion molecules.

The administration timing of the drug to be used in combination is not particularly limited and may be administered simultaneously with the compound (II) and separately at a time interval.

The compound (II) is administered for animals including humans in dosage form suitable for oral or non-oral administration, such as a pharmaceutical composition obtained by blending with an acceptable carrier in view of a pharmaceutical preparation (an excipient, a binding agent, a disintegrator, a flavoring agent, an odor masking agent, an emulsifier, a diluent, a solubilizing agent, etc.) or a pharmaceutical preparation including a tablet, a pill, a powder, a granule, a capsule, a troche, a syrup, a liquid, an emulsion, a suspension, an injection (a liquid, a suspension, etc.), a suppository, an inhalant, a percutaneous absorption agent, an eyedrop and an eye ointment.

When it is administered as a solid preparation, additives may be used, which include sucrose, lactose, cellulose sugar, D-mannitol, maltitol, dextran, starches, agar, alignates, chitins, chitosans, pectines, tragacanth gums, Arabian gums, gelatins, collagens, casein, albumin, calcium phosphate, sorbitol, glycine, carboxymethylcellulose, polyvinylpyrrolidone, hydroxypropyl cellulose, hydroxypropylmethyl cellulose, glycerin, polyethylene glycol, sodium hydrogen carbonate, stearic acid magnesium and talc. Furthermore, if necessary, a tablet may be covered with ordinary coating, for example, a sugar-coating pill, an enteric coating tablet, a film coating tablet or double-layered tablet and a multi-layered tablet may be used.

When it is administered as a semi-solid preparation, an animal/vegetable fat and oil (olive oil, corn oil, castor oil, etc.), mineral fat and oil (vaseline, white vaseline, paraffin wax, etc.), wax (jojoba oil, carnauba wax, beeswax, etc.), partially or completely synthesized glycerin fatty acid ester (lauric acid, myristic acid, palmitic acid, etc.) may be used. Examples of commercially available products of these may include Witepsol (manufactured by Dynamit Nobel) and pharmasole (manufactured by NOF Corporation).

When it is administered as a liquid preparation, additives, for example, may include sodium chloride, glucose, sorbitol, glycerin, olive oil, propylene glycol and ethyl alcohol, etc. In particular, when it is administered as an injection preparation, an aseptic aqueous solution such as a physiological saline solution, an isotonic solution and oily liquid (e.g., sesame oil, bean oil) may be used. Furthermore, if necessary, an appropriate suspending agent such as sodium carboxymethylcellulose, a nonionic surfactant and a solubilizing agent such as benzyl benzoate or benzyl alcohol may be used in combination. Furthermore, when it is administered as an eyedrop, an aqueous liquid or an aqueous solution may be used. In particular, an aseptic aqueous injection solution may be mentioned. To the eyedrop liquid preparation, additives such as a buffer (a borate buffer, an acetate buffer and a carbonate buffer are preferred for reducing irritation), an isotonic agent, a solubilizing agent, a preservative, a viscous agent, chelating agent, a pH regulator (pH is preferably adjusted generally to about 6 to 8.5) and a fragrance may be added appropriately. In these preparations, the amount of an active ingredient is 0.1 to 100% by weight based on the preparation, and properly 1 to 50% by weight. The dose varies depending upon the symptom, weight and age, etc. of the patient. Generally, in the case of oral administration, the dose is about 1 to 500 mg per adult per day. It is preferred that the dose is administered at a time or separately several times.

EXAMPLES

Example 1

As a compound (I) according to the present invention, TsPD represented by the formula (VI) below and TsPDG represented by the formula (VII) were synthesized.

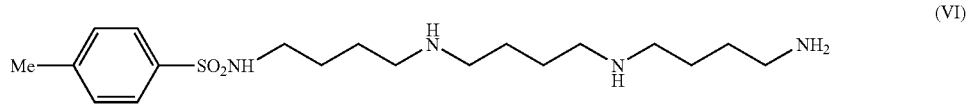

(VI)

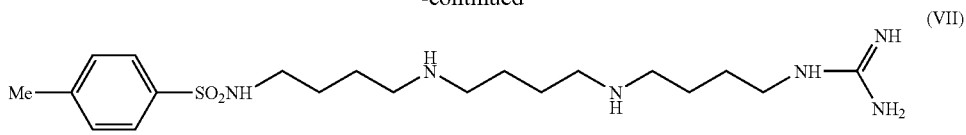

The outline of a synthesis procedure is as follows.

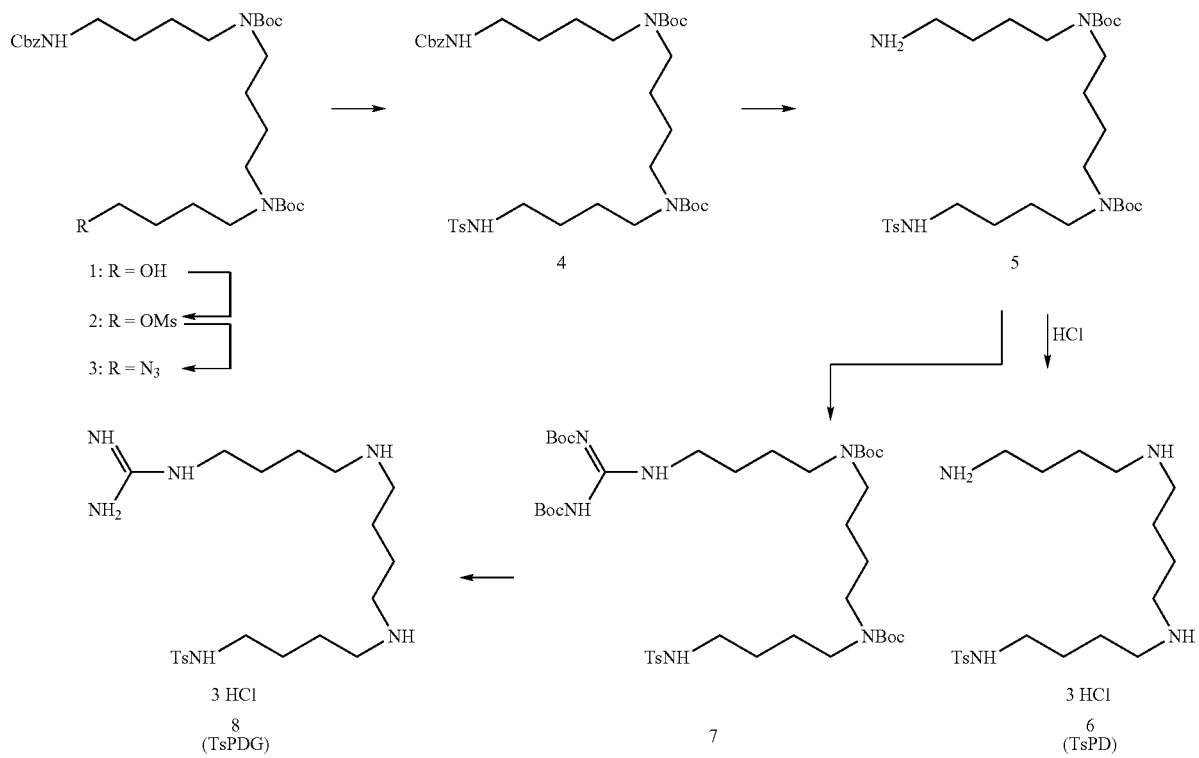

[Compound 1]

Compound 1 can be synthesized by a known method (D. Sengupta, et al., Bioorganic and Medicinal chemistry, 4 (6) 803-813 (1996)).

[Compound 2]

A solution of compound 1 (423 mg, 0.747 mmol), methanesulfonyl chloride (MsCl) (102 mg, 0.89 mmol) and triethylamine (0.42 mL, 3 mmol) in $CH_2Cl_2$ (14 mL) was stirred at 0° C. for 2 hours and thereafter continued to stir at room temperature overnight. The mixture solution was washed with brine and dried over $MgSO_4$ and the solvent was removed under reduced pressure. The residue was purified by silica gel column chromatography (developing solvent: EtOAc:hexane (2:1)) to obtain a colorless oil (598 mg, 93%).

HRMS (FAB) (m/z) Calcd for $C_{31}H_{54}N_4O_9S$: 644.3580

Found: 644.3580

$^1$H NMR (600 MHz, $CDCl_3$) δ: 1.43-1.54 (m, 26H), 1.61-1.65 (m, 2H), 1.70-1.75 (m, 2H), 3.00 (s, 3H), 3.14-3.22 (m, 10H), 4.23-4.25 (m, 2H), 5.09 (s, 2H), 7.31-7.36 b (m, 5H)

[Compound 3]

A mixture solution of compound 2 (350 mg, 0.543 mmol) and $NaN_3$ (52 mg, 0.8 mmol) in DMF (3 ml) was stirred at room temperature overnight. The mixture solution was diluted with EtOAc, washed with water and dried over $MgSO_4$ and the solvent was removed under reduced pressure. The residue was purified by silica gel column chromatography (developing solvent: EtOAc:hexane (1:1)) to obtain a colorless oil (320 mg, 97%).

HRMS (FAB) (m/z) Calcd for $C_{30}H_{51}N_6O_6$: 591.3869

Found: 591.3574

$^1$H NMR (600 MHz, $CDCl_3$) δ: 1.44-1.58 (m, 30H), 3.16-3.23 (m, 10H), 3.28-3.30 (m, 2H), 5.09 (s, 2H), 7.31-7.36 (m, 5H)

[Compound 4]

A solution of compound 3 (184 mg, 031 mmol) in THF (3 mL) was subjected to hydrogenation performed at room temperature for 24 hours under an $H_2$ atmosphere in the presence of 3.5 to 6.5% of a palladium carbon ethylene diamine complex (44 mg) as a catalyst. The catalyst was filtered off through a Celite pad. The filtrate was concentrated to obtain oil. To the solution of the oil in $CH_2Cl_2$ (3 mL), p-toluenesulfonyl chloride (TsCl) (59 mg, 0.31 mmol) and triethylamine (56 µL, 0.4 mmol) were added. The mixture solution was stirred at room temperature. Eighteen hours later, the mixture solution was diluted with $CH_2Cl_2$, washed with brine and dried over $MgSO_4$ and the solvent was distilled away under reduced pressure. The residue was purified by silica gel column chromatography (developing solvent: EtOAc:hexane (1:1)) to obtain a colorless oil (150 mg, 67%).

HRMS (FAB) (m/z) Calcd for $C_{37}H_{59}N_4O_8S$: 719.4053
Found: 719.4054
$^1$H NMR (600 MHz, CDCl$_3$) δ: 1.43-1.53 (m, 30H), 2.42 (s, 3H), 2.92-2.95 (m, 2H), 3.10-3.23 (m, 10H), 5.09 (s, 2H), 7.28-7.35 (m, 7H), 7.74 (d, 2H, J=8.22 Hz)
[Compound 5]

A solution of compound 4 (202 mg, 0.28 mmol) in THF (3 mL) was subjected to hydrogenation performed at room temperature for 24 hours under an H$_2$ atmosphere in the presence of 10% of a palladium carbon (40 mg) as a catalyst. The catalyst was filtered off through a Celite pad. The filtrate was concentrated under reduced pressure. The residue was purified by silica gel column chromatography (developing solvent: CHCl$_3$:MeOH:25% NH$_4$OH (100:20:2)) to obtain a colorless oil (72 mg, 44%).

HRMS (FAB) (m/z) Calcd for $C_{29}H_{53}N_4O_6S$: 585.3685
Found: 585.3683
$^1$H NMR (600 MHz, CDCl$_3$) δ: 1.43-1.54 (m, 30H), 2.42 (s, 3H), 2.62-2.67 (m, 2H), 2.93-2.96 (m, 2H), 3.11-3.23 (br, 8H), 7.30 (d, 2H, J=7.92 Hz), 7.75 (dd, 2H, J=8.58, 2.1 Hz)
[Compound 6 (TsPD)]

To a solution of compound 5 (62 mg, 0.106 mmol) in THF (2 mL), concentrated HCl (0.2 mL) was added. The mixture solution was stirred at room temperature for 24 hours and concentrated under reduced pressure to obtain a white powder (52 mg, 100%).

HRMS (FAB) (m/z) Calcd for $C_{19}H_{37}N_4O_2S$: 385.2637 [M-3HCl+1]
Found: 385.2642
$^1$H NMR (600 MHz, D$_2$O) δ: 1.51-1.57 (m, 12H), 2.24 (s, 3H), 2.72 (t, 2H, J=6.9 Hz), 2.85-2.89 (m, 8H), 3.42 (t, 2H, J=6.18 Hz), 7.28 (d, 2H, J=8.22 Hz), 7.56 (d, 2H, 8.22 Hz)
[Compound 7]

A solution of compound 5 (115 mg, 0.196 mmol) and 1,3-bis(tert-butoxycarbonyl)-2-methyl-2-thiopseudourea (57 mg, 0.196 mmol) in CH$_2$Cl$_2$ (2 mL) was stirred at room temperature for 48 hours. The mixture solution was filtrated through a Cerite pad, and the filtrate was concentrated under reduced pressure. The residue was purified by silica gel column chromatography (developing solvent: EtOAc:hexane (1:1)) to obtain a colorless oil (135 mg, 83%).

HRMS (FAB) (m/z) Calcd for $C_{40}H_{71}N_6O_{10}S$: 827.4951
Found: 827.4967
$^1$H NMR (600 MHz, CDCl$_3$) δ: 1.41-1.59 (m, 48H), 2.43 (s, 3H), 2.94-2.96 (m, 2H), 3.10-3.21 (m, 8H), 3.41-3.44 (m, 2H), 7.30 (d, 2H, J=8.22), 7.75 (d, 2H, J=8.22 Hz), 8.35 (br s, 1H), 11.50 (s, 1H)
[Compound 8 (TsPDG)]

To a solution of compound 7 (116 mg, 0.14 mmol) in THF (2 mL), concentrated HCl (0.5 mL) was added. The mixture solution was stirred at room temperature for 24 hours and concentrated under a reduced pressure to obtain a white powder (75 mg, 100%).

HRMS (FAB) (m/z) Calcd for $C_{20}H_{39}N_6O_2S$: 427.2855 [M-3HCl+1]
Found: 427.2854
$^1$H NMR (600 MHz, D$_2$O) δ: 1.31-1.36 (m, 2H), 1.44-1.57 (m, 10H), 2.24 (s, 3H), 2.73 (t, 2H, J=6.9 Hz), 2.80-2.82 (m, 2H), 2.85-2.88 (m, 6H), 3.02 (t, 2H, J=6.9 Hz), 7.28 (d, 2H, J=8.22 Hz), 7.56 (d, 2H, J=8.22 Hz)

Example 2

As a compound (I) according to the present invention, TsSPMG represented by the formula (V) below was synthesized.

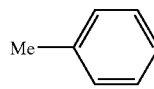

The outline of a synthesis procedure is as follows.

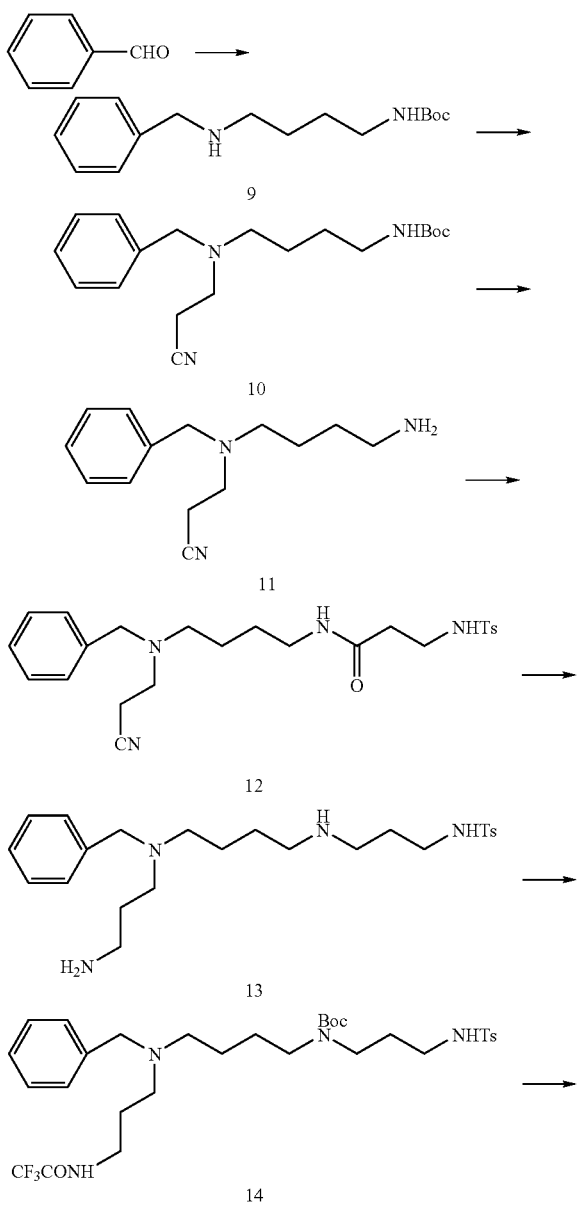

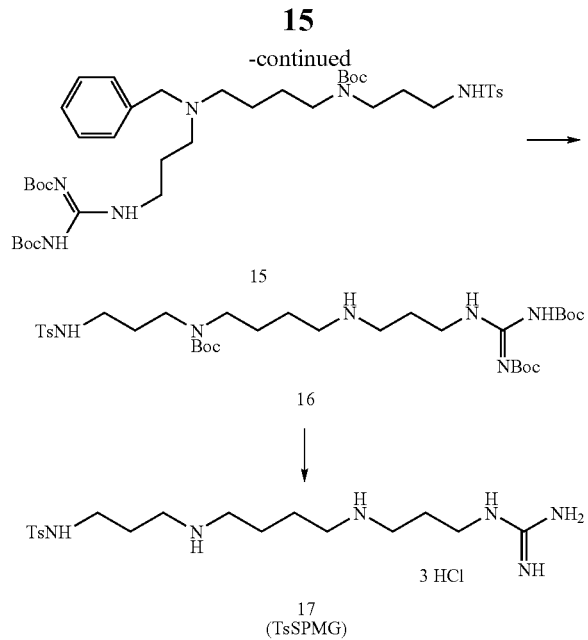

[Compound 9]

A mixture solution of benzaldehyde (1.06 g, 10 mmol) and tert-butyl ester (1.88 g, 10 mmol) of N-4-aminobutyl)carbamic acid in MeOH (25 mL) was stirred at room temperature. Subsequently, MgSO$_4$ (1.8 g) was added and the mixture solution was continued to stir at room temperature for one hour. The mixture solution was cooled to 0° C. and NaBH$_4$ (2.65 g, 70 mmol) was added by split addition for one hour. MeOH (15 mL) was further added and stirred to obtain a suspension solution. Stirring was further continued for 12 hours and the reaction solution was filtrated and then concentrated. EtOAc (100 mL) was added to the residue and the suspension solution was stirred for 0.5 hours and then filtrated. The filtrate was washed with water and dried over MgSO$_4$ and EtOAc was distilled away under reduced pressure. The residue was purified by silica gel column chromatography (developing solvent: CHCl$_3$:MeOH:25% NH$_4$OF (100:10:1)) to obtain a colorless oil (2.45 g, 88%).

HRMS (FAB) (m/z) Calcd for C$_{16}$H$_{27}$N$_2$O$_2$: 279.2072
Found: 279.2071

$^1$H NMR (600 MHz, CDCl$_3$) δ: 1.43 (s, 9H), 1.53-1.55 (m, 4H), 2.65 (t, 2H, J=6.5 Hz), 3.12-3.13 (m, 2H), 3.78 (s, 2H), 4.83 (br s, 1H), 7.24-7.26 (m, 1H), 7.31-7.33 (m, 4H)

[Compound 10]

A mixture solution of compound 9 (2.41 g, 8.66 mmol) and acrylonitrile (732 mg, 13.8 mmol) in MeOH (10 mL) was stirred at 80° C. for 6 hours. Thereafter, the mixture solution was concentrated and purified by silica gel column chromatography (developing solvent: EtOAc:hexane (1:1)) to obtain a colorless oil (2.87 g, 100%).

HRMS (FAB) (m/z) Calcd for C$_{19}$H$_{30}$N$_3$O$_2$: 332.2337
Found: 332.2340

$^1$H NMR (600 MHz, CDCl$_3$) δ: 1.44 (s, 9H), 1.49-1.51 (m, 4H), 2.41 (t, 2H, J=6.5 Hz), 2.51 (t, 2H, J=6.9 Hz), 2.77 (t, 2H, J=6.9 Hz), 3.09-3.10 (br, 2H), 3.60 (s, 2H), 4.60 (br s, 1H), 7.26-7.27 (m, 1H), 7.32-7.33 (m, 4H)

[Compound 11]

To a solution of compound 10 (2.82 g, 8.5 mmol) in THF (10 mL), concentrated hydrochloric acid (3 mL) was added. The mixture solution was stirred at room temperature for 24 hours and concentrated under reduced pressure. The residue was diluted with EtOAc and water. After the aqueous phase was washed with EtOAc and separated, and then made basic to pH 11 with 25% NH$_4$OH. The mixture solution was extracted with EtOAc, washed with water and dried over Na$_2$SO$_4$ and EtOAc was removed under reduced pressure. The residue was purified by silica gel column chromatography (developing solvent: CHCl$_3$:MeOH:25% NH$_4$OH (100:40:4)) to obtain a colorless oil (1.86 g, 95%).

HRMS (FAB) (m/z) Calcd for C$_{14}$H$_{22}$N$_3$: 232.1813
Found: 232.1818

$^1$H NMR (600 MHz, CDCl$_3$) δ: 1.45-1.48 (m, 2H), 1.51-1.54 (m, 2H), 2.40 (t, 2H, J=6.9 Hz), 2.51 (t, 2H, J=6.9 Hz), 2.67 (t, 2H, J=7.2 Hz), 2.79 (t, 2H, J=7.2 Hz), 3.61 (s, 2H), 7.25-7.28 (m, 1H), 7.31-7.34 (m, 4H)

[Compound 12]

A mixture solution of compound 11 (0.93 g, 4 mmol), N-[(4-(methylphenyl)sulfonyl]-β-alanine (0.97 g, 4 mmol) and 4,6-dimethoxy-1,3,5-triazin-2-yl)methylmorpholinium chloride) (DMT-MM) (1.106 g, 4 mmol) in MeCN (60 mL) was stirred at room temperature for 24 hours. The mixture solution was concentrated and the residue was diluted with EtOAc, washed with water, dried over MgSO$_4$ and concentrated under reduced pressure. The residue was purified by silica gel column chromatography (developing solvent: EtOAc:CHCl$_3$ (3:1)) to obtain a colorless oil (1.287 g, 70%).

HRMS (FAB) (m/z) Calcd for C$_{24}$H$_{33}$N$_4$O$_3$S: 457.2273
Found: 457.2271

$^1$H NMR (600 MHz, CDCl$_3$) δ: 1.49-1.62 (m, 4H), 2.38 (t, 2H, J=5.5 Hz), 2.40-2.43 (m. 5H), 2.50 (t, 2H, J=6.5 Hz), 2.77 (t, 2H, J=6.5 Hz), 3.14-3.17 (m, 2H), 3.18-3.21 (m, 2H), 3.60 (s, 2H), 5.50 (br s, 1H), 5.76 (br s, 1H), 7.25-7.28 (m, 1H), 7.30 (d, 2H, J=7.9 Hz), 7.27-7.33 (m, 4H), 7.74 (d, 2H, J=7.9 Hz)

[Compound 13]

A mixture solution of compound 12 (1.21 g, 2.65 mmol) and 10M BH$_3$.DMS (4 mL, 40 mmol) in THF (40 mL) was stirred at 80° C. for 24 hours. Thereafter, the mixture solution was cooled to room temperature and a 0.7M HCl-MeOH solution was added thereto. The reaction solution was refluxed for 0.5 hours and evaporated under reduced pressure. The residue was made basic to pH 11 with excess 25% NH$_4$OH. The mixture solution was extracted with CH$_2$Cl$_2$, washed with water and dried over Na$_2$SO$_4$. After the solvent was removed, the residue was purified by silica gel column chromatography (developing solvent: CHCl$_3$:MeOH:25% NH$_4$OH (10:30:3)) to obtain a colorless oil (1.153 g, 97%).

HRMS (FAB) (m/z) Calcd for C$_{24}$H$_{39}$N$_4$O$_2$S: 447.2793
Found: 447.2792

$^1$H NMR (600 MHz, CDCl$_3$) δ: 1.47-1.55 (m, 4H), 1.60-1.66 (m, 4H), 2.41 (s, 3H), 2.43 (t, 2H, J=6.54 Hz), 2.48 (t, 2H, J=6.9 Hz), 2.53 (t, 2H, J=6.9 Hz), 2.67 (t, 2H, J=5.8 Hz), 2.74 (t, 2H, J=6.54 Hz), 3.03 (t, 2H, J=5.82 Hz), 3.54 (s, 2H), 7.23-7.25 (m, 1H), 7.28 (d, 2H, J=8.22), 7.30-7.32 (m, 4H), 7.74 (d, 2H, J=8.22 Hz)

[Compound 14]

A mixture solution of compound 13 (828 mg, 1.85 mmol) and trifluoroethyl acetate (263 mg, 1.85 mmol) in THF (50 mL) was stirred at 0° C. Three hours later, (Boc)$_2$O (404 mg, 1.85 mmol) was added to the reaction solution. After stirring for 3 hours, the solvent was removed under reduced pressure. The residue was dissolved in EtOAc, washed with water and dried over $Na_2SO_4$. After the solvent was removed under reduced pressure, the residue was purified by silica gel column chromatography (developing solvent: $CHCl_3$:MeOH (20:1)) to obtain a colorless oil (1.11 g, 93%).

HRMS (FAB) (m/z) Calcd for $C_{31}H_{46}N_4O_5F_3S$: 643.3140
Found: 643.3180

$^1$H NMR (600 MHz, $CDCl_3$) δ: 1.38-1.46 (m, 13H), 1.64-1.72 (br, 4H), 2.40 (s, 3H), 2.45 (br s, 2H), 2.55 (br s, 2H), 2.84-2.94 (br, 2H), 3.00-3.15 (br, 2H), 3.16-3.24 (br, 2H), 3.31-3.33 (m, 2H), 3.53 (s, 2H), 6.04 (br s, 1H), 7.23-7.33 (m, 7H), 7.74 (d, 2H, J=8.28 Hz), 8.52 (br s, 1H)

[Compound 15]

To a solution of compound 14 (469 mg, 0.73 mmol) in MeOH (15 mL) and water (2.5 mL), potassium carbonate (442 mg, 3.2 mmol) was added. The reaction solution was refluxed for 12 hours and cooled, and the solvent was removed under reduced pressure. The residue was dissolved in EtOAc, washed with water and dried over $Na_2SO_4$. After the solvent was removed under reduced pressure to obtain a colorless oil, that is, crude amine. An ice cooled solution of crude amine in $CH_2Cl_2$ (5 mL), 1,3-bis(tert-butoxycarbonyl)-2-methyl-2-thiopseudourea (316 mg, 1.09 mmol) was added. After stirring for 12 hours, the mixture solution was concentrated under reduced pressure. The residue was purified by silica gel column chromatography (developing solvent: $CHCl_3$:MeOH (20:1)) to obtain a colorless oil (574 mg, 100%).

HRMS (FAB) (m/z) Calcd for $C_{40}H_{65}N_6O_8S$: 789.4584
Found: 789.4584

$^1$H NMR (600 MHz, $CDCl_3$) δ: 1.36-1.60 (m, 35H), 2.36-2.46 (m, 9H), 2.85 (br s, 2H), 2.96 (br s, 2H), 3.20 (br s, 2H), 3.51 (s, 2H), 3.00-3.15 (br, 2H), 7.26-7.29 (m, 7H), 7.73 (dd, 2H, J=8.28, 3.0 Hz), 8.37 (br s, 1H), 11.48 (br s, 1H)

[Compound 16]

A solution of compound 15 (252 mg, 0.32 mmol) in THF (5 mL) was subjected to hydrogenation performed at room temperature for 24 hours under an $H_2$ atmosphere in the presence of 10% of Pd—C (100 mg) as a catalyst. The catalyst was filtered off through a Celite pad. The filtrate was concentrated and dried. The residue was purified by silica gel column chromatography (developing solvent: $CHCl_3$:MeOH (20:1→10:1)) to obtain a colorless oil (70 mg, 32%).

HRMS (FAB) (m/z) Calcd for $C_{33}H_{59}N_6O_8S$: 699.4114
Found: 699.4114

$^1$H NMR (600 MHz, $CDCl_3$) δ: 1.40 (br s, 9H), 1.48 (s, 9H), 1.51 (s, 9H), 1.52-1.80 (m, 8H), 2.40 (s, 3H), 2.87-3.11 (m, 8H), 3.24-3.28 (m, 2H), 3.55-3.57 (m, 2H), 7.26-7.28 (m, 2H), 7.76-7.80 (m, 2H), 8.71 (t, 1H, J=5.8 Hz), 11.46 (s, 1H)

[Compound 17 (TsSPMG)]

To a solution of compound 16 (70 mg, 0.1 mmol) in THF (2 mL), concentrated hydrochloric acid (0.2 mL) was added. The mixture solution was stirred at room temperature for 24 hours, concentrated under reduced pressure to obtain amorphous white powder (50 mg, 100%).

HRMS (FAB) (m/z) Calcd for $C_{18}H_{35}N_6O_2S$: 399.2541 [M-3HCl+1]
Found: 399.2542

$^1$H NMR (600 MHz, $D_2O$) δ: 1.55-1.58 (m, 4H), 1.64-1.69 (m, 2H), 1.76-1.81 (m, 2H), 2.24 (s, 3H), 2.80 (t, 2H, J=6.9 Hz), 2.86-2.93 (m, 8H), 3.10 (t, 2H, J=6.9 Hz), 7.28 (d, 2H, J=8.22 Hz), 7.56 (d, 2H, J=8.22 Hz)

Example 3

As a compound (I) according to the present invention, BsPDG represented by the formula (VIII) below was synthesized.

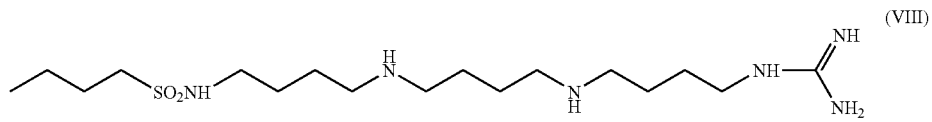

The outline of a synthesis procedure is as follows.

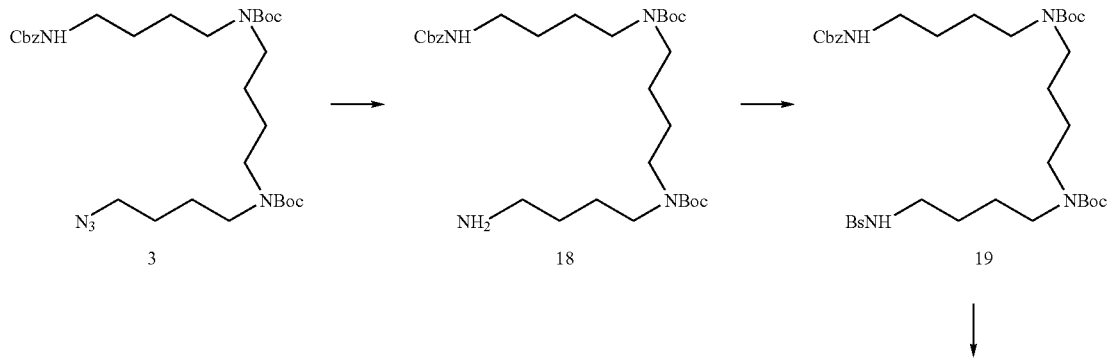

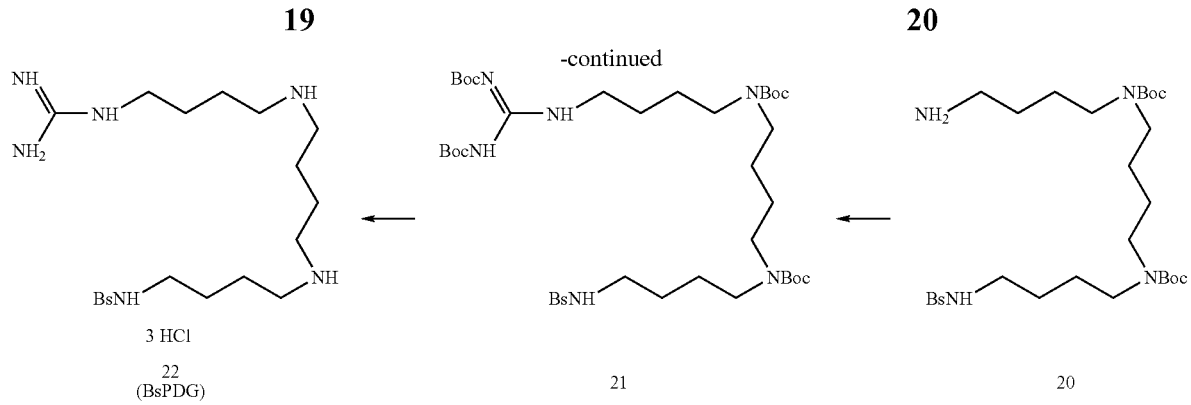

[Compound 3]

Compound 3 is identical with the compound of Example 2 described above, explanation will be omitted herein

[Compound 18]

A solution of compound 3 (1.71 g, 2.89 mmol) in THF (30 mL) was subjected to hydrogenation by placing it at room temperature for 24 hours under an $H_2$ atmosphere in the presence of a 3.5-6.5% of a palladium carbon ethylenediamine complex (171 mg) as a catalyst. The catalyst was filtered off through a Celite pad. The filtrate was concentrated to obtain oil. The residue was purified by silica gel column chromatography (developing solvent: $HCl_3$:MeOH:25% $NH_4OH$ (100:20:2)) to obtain a colorless oil (1.14 g, 70%).

HRMS (FAB) (m/z) Calcd for $C_{30}H_{53}N_4O_6$: 565.3964
Found: 565.3968
$^1$H NMR (600 MHz, $CDCl_3$) δ: 1.44-1.55 (m, 30H), 3.17-3.21 (m, 12H), 5.09 (s, 2H), 7.30-7.33 (m, 1H), 7.35-7.36 (m, 4H)

[Compound 19]

To a solution of compound 19 (465 mg, 0.823 mmol) in $CH_2Cl_2$ (10 mL), 1-butanesulfonyl chloride (BsCl) (129 mg, 0.823 mmol) and triethylamine (0.15 mL, 1.07 mmol) were added. The mixture solution was stirred at room temperature. Eighteen hours later, the mixture solution was diluted with $CH_2Cl_2$, washed with brine, dried over $MgSO_4$ and concentrated under reduced pressure. The residue was purified by silica gel column chromatography (developing solvent: EtOAc:hexane (1:1)) to obtain a colorless oil (309 mg, 55%).

HRMS (FAB) (m/z) Calcd for $C_{34}H_{61}N_4O_8S$: 685.4209
Found: 685.4204
$^1$H NMR (600 MHz, $CDCl_3$) δ: 0.95 (t, 3H, J=7.56 Hz), 1.76-1.81 (m, 12H), 2.98-3.02 (m, 2H), 3.10-3.24 (m, 12H), 5.09 (s, 2H), 7.30-7.32 (m, 1H), 7.35-7.36 (m, 4H)

[Compound 20]

A solution of compound 19 (240 mg, 0.35 mmol) in THF (3 mL) was subjected to hydrogenation by placing it at room temperature for 48 hours under an $H_2$ atmosphere in the presence of a 10% of a palladium carbon (48 mg) as a catalyst. The catalyst was filtered off through a Celite pad. The filtrate was concentrated. The residue was purified by silica gel column chromatography (developing solvent: $CHCl_3$:MeOH: 25% $NH_4OH$ (100:20:2)) to obtain a colorless oil (135 mg, 70%).

HRMS (FAB) (m/z) Calcd for $C_{26}H_{55}N_4O_6S$: 551.3842
Found: 551.3837
$^1$H NMR (600 MHz, $CDCl_3$) δ: 0.95 (t, 3H, J=7.56 Hz), 1.44-1.55 (m, 32H), 1.76-1.81 (m, 2H), 2.99-3.02 (m, 2H), 3.10-3.25 (m, 12H)

[Compound 21]

A solution of compound 19 (123 mg, 0.22 mmol) and 1,3-bis(tert-butoxycarbonyl)-2-methyl-2-thiopseudourea (64 mg, 0.196 mmol) in $CH_2Cl_2$ (4 mL) was stirred at room temperature for 48 hours. The mixture solution was concentrated under reduced pressure. The residue was purified by silica gel column chromatography (developing solvent: $CH_2Cl_2$ and EtOAc) to obtain a colorless oil (60 mg, 34%).

HRMS (FAB) (m/z) Calcd for $C_{37}H_{73}N_6O_{10}S$: 793.5108
Found: 793.5109
$^1$H NMR (600 MHz, $CDCl_3$) δ: 0.95 (t, 3H, J=7.56 Hz), 1.44-1.60 (m, 50H), 1.78-1.80 (m, 2H), 2.99-3.02 (m, 2H), 3.12-3.25 (m, 2H), 3.12-3.25 (m, 12H), 8.34 (br s, 1H), 11.50 (s, 1H)

[Compound 22 (BsPDG)]

To a solution of compound 21 (50 mg, 0.063 mmol) in THF (0.5 mL), concentrated HCl (0.2 mL) was added. The mixture solution was stirred at room temperature for 24 hours and concentrated under reduced pressure to obtain a white powder (31 mg, 100%).

HRMS (FAB) (m/z) Calcd for $C_{17}H_{41}N_6O_2S$: 393.3011 [M-3HCl+1]
Found: 393.3012
$^1$H NMR (600 MHz, $D_2O$) δ: 0.72 (t, 3H, J=7.56 Hz), 1.25 (sex, 2H, J=7.56 Hz), 1.40-1.49 (m, 4H), 1.50-1.59 (m, 10H), 2.86-2.89 (m, 8H), 2.92 (t, 2H, J=6.84 Hz), 3.00-3.04 (m, 4H)

Example 4

To confirm pharmacological function of TsPD, TsPDG, TsSPMG, BsPDG, and Tosyl-SPM synthesized above (synthesized by the method described in Patent Document 1 mentioned above), the effect of these compounds on NMDA receptor was measured by a two-electrode voltage clamp method.

(1) Preparation of Xenopus Oocyte Having NMDA Receptor Expressed Therein

The scheme of experimental example for expressing an oocyte is shown in FIG. 1. This method can be carried out in accordance with the method of Masuko et al. (Masuko T. et al., Mol. Pharmacol. 55: 957-969 (1999); Masuko T. et al., Nuerosci. Lett. 371: 30-33 (2004); Masuko T. et al., Chem. Pharm. Bull. 53 (4) 444-447 (2005)). To the oocyte, cRNAs of an NR1 subunit and an NR2 subunit of NMDA receptor were injected in a ratio of 1:5 (NR1: 0.1 to 4 ng, NR2: 0.5 to 20 ng) to obtain the oocyte in which NMDA receptor was expressed.

The oocytes were cultured in a medium (96 mM NaCl, 2 mM KCl, 1 mM $MgCl_2$, 1.8 mM $CaCl_2$, 5 mM Na-HEPES, 2.5 mM sodium pyruvate, 50 μg/ml gentamicin, pH=7.5) at 19° C. for 1 to 3 days.

At the measurement date, K$^+$-BAPTA was injected in the oocytes and then, the activity of the receptors was measured by the two-electrode voltage clamp method (described later) using a recording buffer (96 mM NaCl, 2 mM KCl, 1.8 mM BaCl$_2$, 10 mM Na-HEPES, pH=7.5).

Note that there is a single type of gene in NR1 and 4 types of genes, namely NR2A to NR2D, in NR2. There are NR1/NR2A, NR1/NR2B, NR1/NR2C and NR1/NR2D subtypes in NMDA receptor. However, NR1/NR2A and NR1/NR2B subtypes are conceivably present widely in the brain. Therefore, the activity inhibitory effects on these two types were measured in the following experiments.

(2) Two-Electrode Voltage Clamp Method

The two-electrode voltage clamp method was carried out in accordance with the method of Williams et al. (Williams, K. et al., Mol. Pharmacol 38: 85-108). The current flowing through the entire membrane of the oocyte was measured by an amplifier CEZ-1250 (Nihon Kohden Corporation) for the two-electrode voltage clamp method. The electrode was filled with 3M potassium chloride and the resistance was set at 0.4 to 4 MΩ. In measurement, glutamate and glycine were added as NMDA agonists.

(3) Measurement of Effect of TsPD, TsPDG, TsSPMG, BsPDG and Tosyl-SPM Upon NMDA Receptor (NR1/NR2A and NR1/NR2B)

To the oocytes obtained by the aforementioned method, various concentrations of TsPD, TsPDG, TsSPMG, BsPDG and Tosyl-SPM were added. The activity inhibitory effect on NMDP receptor subtypes was measured at a fixed voltage (Vh) of −70 mV (resting membrane potential).

As a comparative example, the same measurement is performed by use of Dansyl-SPM represented by the aforementioned formula (III).

Values obtained from 4 to 5 oocytes were averaged. The average value±S.E.M. was regarded as a measurement value. The results are shown in FIG. 2. IC$_{50}$ values obtained from these results are shown in Table 1.

TABLE 1

|  | NR1/NR2A(μM) | NR1/NR2B(μM) |
| --- | --- | --- |
| Tosyl-SPM | 0.35 ± 0.01 | 0.40 ± 0.01 |
| TsSPMG | 0.32 ± 0.03 | 0.37 ± 0.05 |
| TsPD | 0.074 ± 0.003 | 0.15 ± 0.001 |
| TsPDG | 0.017 ± 0.002 | 0.027 ± 0.002 |
| BsPDG | 0.015 ± 0.001 | 0.024 ± 0.003 |
| Dansyl-SPM | 0.27 ± 0.03 | 0.31 ± 0.03 |

As shown in FIG. 2 and Table 1, Tosyl-SPM, TsSPMG, TsPD, TsPDG, BsPDG each shows good NMDA receptor activity inhibitory effect. Particularly, TsPD, TsPDG and BsPDG, more particularly, TsPDG and BsPDG exhibit extremely excellent effects. In consideration of IC$_{50}$ (1 μM) of memantine, which has been known as a therapeutic drug for Alzheimer's disease, high receptor-activity inhibitory effect was found to be obtained in a low concentration.

Example 5

A cytotoxicity test was carried out with respect to TsPD, TsPDG, TsSPMG, BsPDG and Tosyl-SPM. Also in this test, Dansyl-SPM was used in a comparative example.

(1) Cell Culture

SH-SY5Y neuroblastoma cell line was purchased from the American Type Culture Collection. The cells were cultured in a D-MEM medium to which penicillin (100 U/ml), streptomycin (100 U/ml) and inactivated fetal bovine serum (Gibco) were added. The cells were maintained in a CO$_2$ incubator at 37° C. and kept under the condition of 95% air and 5% CO$_2$.

(2) Alamar Blue Assay

Undifferentiated SH-SY5Y cells were exposed to various concentrations of polyamine derivatives for 24 hours. An Alamar blue stock solution was transferred to a 96 well plate. The final assay volume was set at 100 μl/well and the final concentration of the Alamar blue was set at 10%. Six hours later, reduced Alamar blue was measured at a wavelength of 570 nm (FIG. 3). A survival rate (%) of the cells exposed to a polyamine derivative for 24 hours was expressed by a relative value of respiratory activity of the cells based on respiratory activity (100%) of mitochondria of the cells to which no drug is added. The concentration of a polyamine derivative at which respiratory activity is 50% is determined as IC$_{50}$ and shown in Table 2.

TABLE 2

|  | IC$_{50}$ |
| --- | --- |
| Tosyl-SPM | 336 ± 7 |
| TsSPMG | 2639 ± 37 |
| TsPD | 1833 ± 46 |
| TsPDG | 2868 ± 66 |
| BsPDG | >3000 |
| Dansyl-SPM | 30 ± 1 |

As shown in Table 2, it was confirmed that TsPD, TsPDG, TsSPMG, BsPDG and Tosyl-SPM have extremely low cytotoxicity as compared to Dansyl-SPM. In consideration of IC$_{50}$ of memantine (110 to 120 μM), the safety of polyamine derivatives according to the present invention is found to be extremely high.

Example 6

Next, the protective effect of polyamine derivatives against nerve cell death due to excitotoxicity was investigated. Rat hippocampal primary culture cells were cultured for seven days and exposed to glutamate or NMDA for one hour. Nerve cell death induced in this manner was evaluated based on lactate dehydrogenase release after 24 hours as an index, significant cell death was observed. In addition, it was observed that nerve cell death caused by glutamate and NMDA exposure has concentration dependency.

The results are shown in FIG. 4.

The nerve cell death induced by glutamate was significantly suppressed by 1 μM TsPDG, 1 μM BsPDG or 10 μM TsPD. The suppression effect of these compounds on nerve cell death was equal to or higher than 30 μM memantine.

The nerve cell death induced by NMDA was also completely suppressed by 1 μM TsPDG, 1 μM BsPDG, or 10 μM TsPD. The suppression effect of these compounds on nerve cell death was higher than 30 μM memantine.

Example 7

Polyamine derivatives according to the present invention were evaluated for permeability through the blood brain barrier.

When 100 mg/kg NMDA was injected into a mouse abdominal cavity, convulsion is induced several minutes later. Then, the convulsion suppression effect of a polyamine derivative on mouse convulsion induced by NMDA was investigated. The results are shown in Table 5.

When 0.5 mg/kg TsPDG and BsPDG were intravenously administered into a mouse 30 minutes before NMDA injection, the time of convulsion induced by NMDA was reduced by 43% and 39%. This reduction rate of convulsion time was equivalent to that (38%) when 10 mg/kg memantine intravenously administered.

From the results, it was demonstrated that TsPDG and BsPDG have a blood function protecting effect and has permeability through the blood blain barrier.

From the foregoing, it was confirmed that polyamine derivatives according to the present invention are excellent in all respects of NMDA receptor activity inhibition, cytotoxicity and nerve cell protection effect as compared to a conventional Alzheimer's disease therapeutic drug, memantine.

Figure 1:
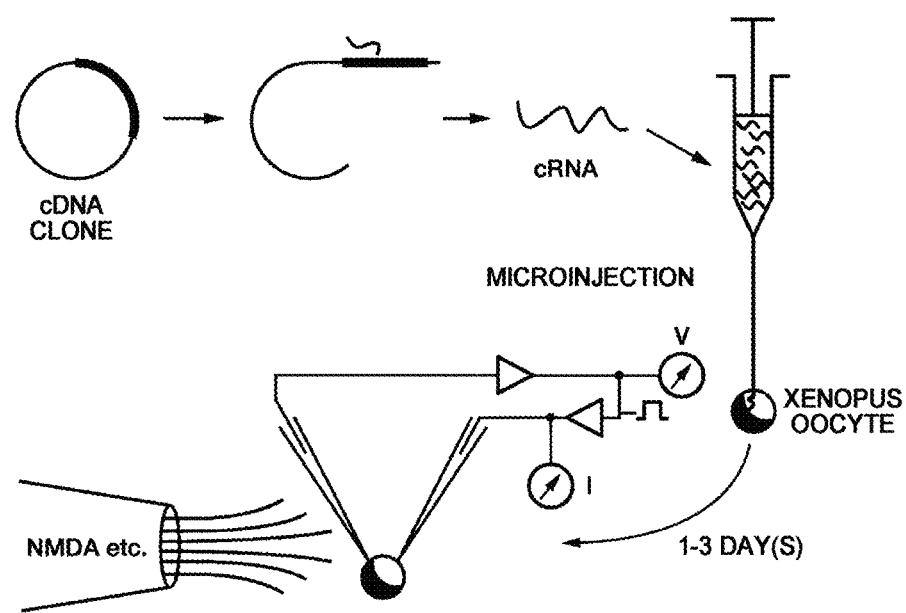
FIG. 1 shows outline of an NMDA receptor expression test in an oocyte.
Figure 2:
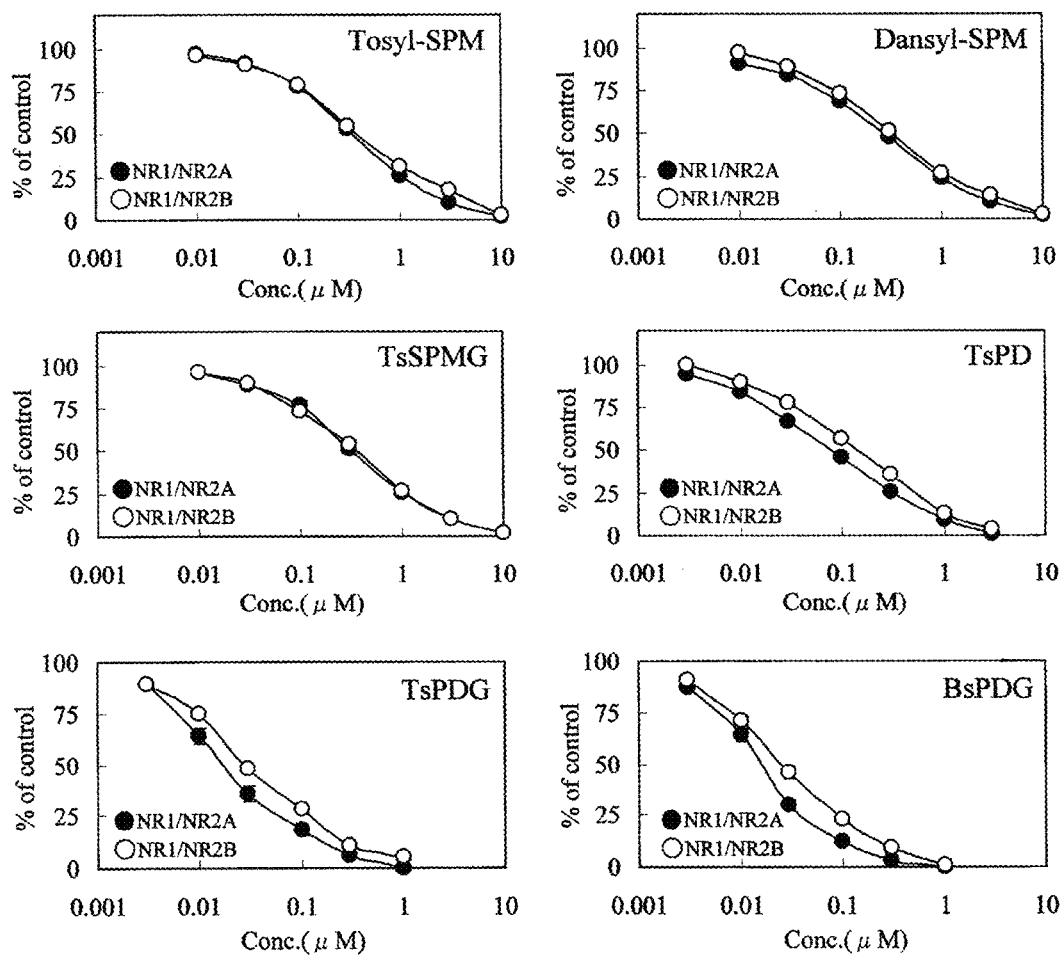
FIG. 2 shows measurement results of NMDA receptor activity inhibitory effect by polyamine derivatives according to the present invention.
Figure 3:
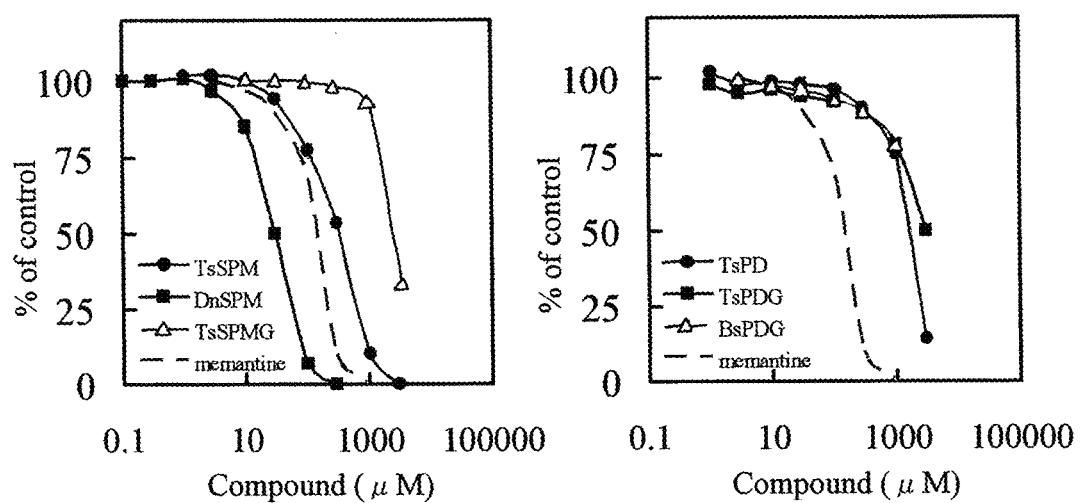
FIG. 3 shows the results of absorption at 570 nm in the presence of Alamar blue after various concentrations of polyamine derivatives were exposed to SH-SY5Y culture cells for 24 hours.
Figure 4:
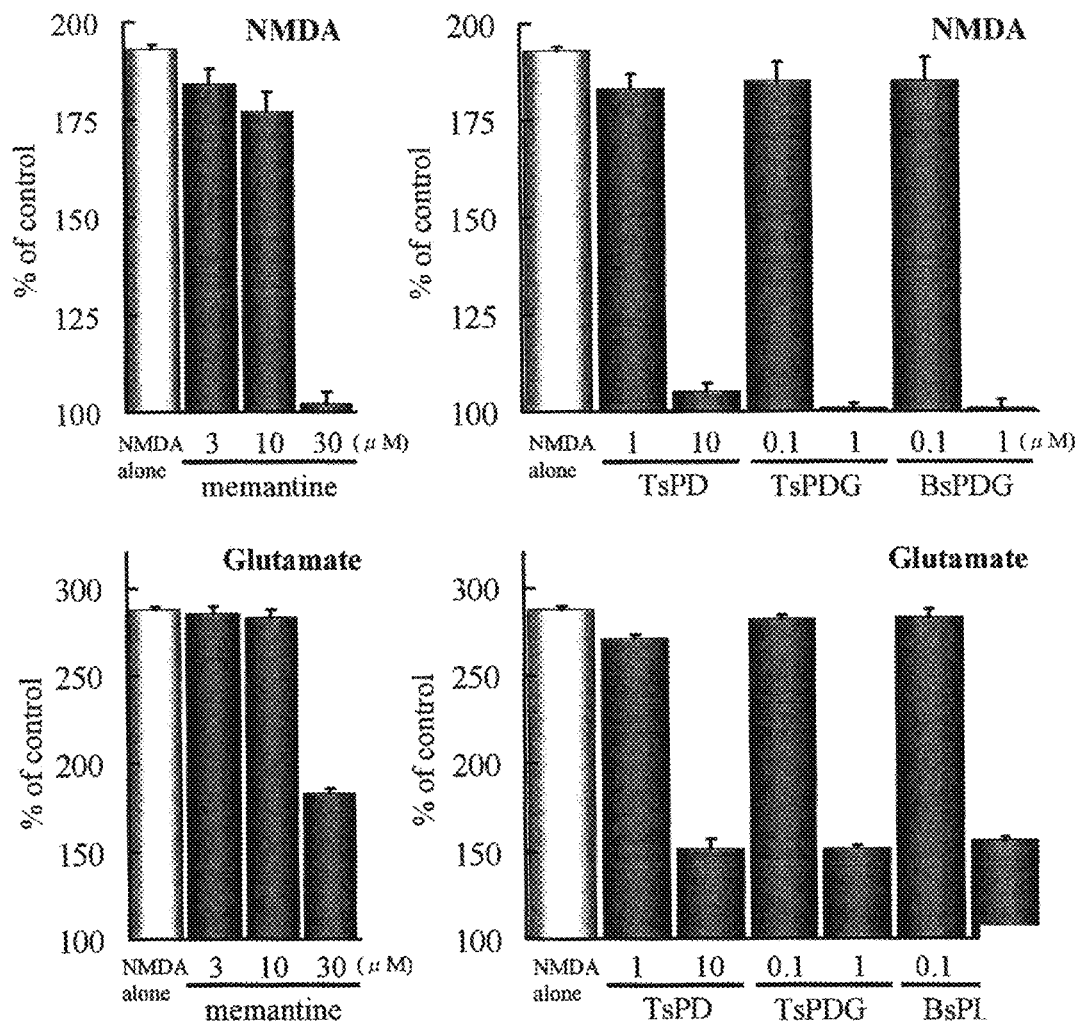
FIG. 4 shows the measurement results of protection effect of polyamine derivatives according to the present invention against nerve cell death due to excitotoxicity.
Figure 5:
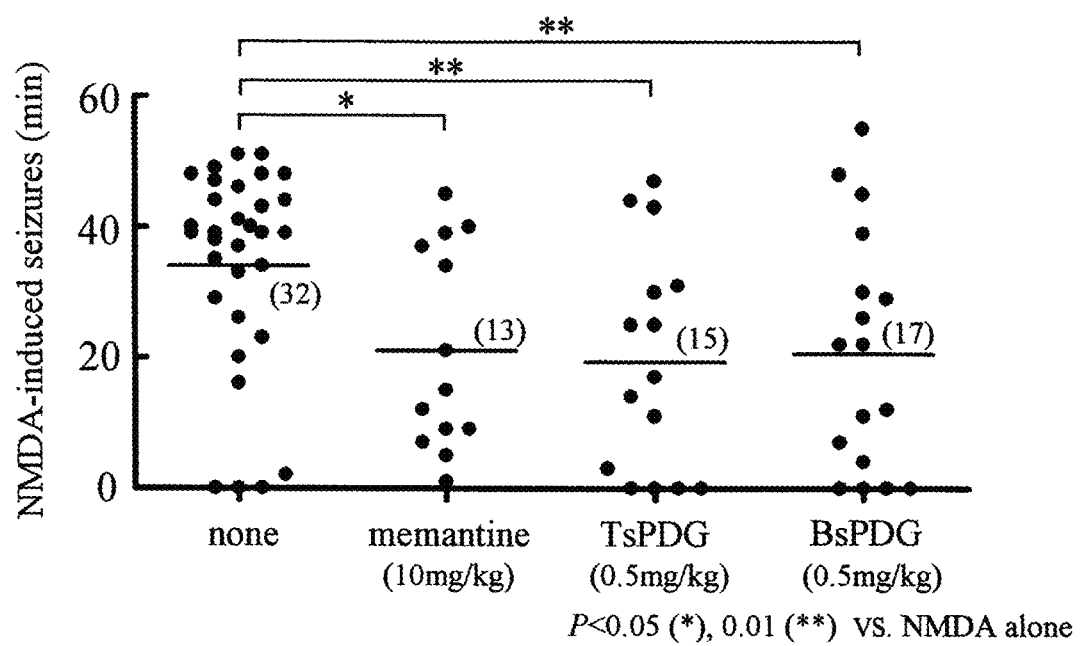
FIG. 5 shows the measurement results of permeability of polyamine derivatives according to the present invention through the blood blain barrier.

The invention claimed is:

1. A compound having the general formula (I) or a pharmacologically acceptable salt thereof:

X—NH—Y—NH—R$^1$  (I)

wherein
X represents an optionally substituted lower alkyl-SO$_2$-group;
Y represents a group selected from the group consisting of —R$^3$—NH—R$^4$—, —R$^5$—NH—R$^6$—NH—R$^7$—, —R$^8$—NH—R$^9$—NH—R$^{10}$—NH—R$^{11}$—and —R$^{12}$—NH—R$^{13}$—NH—R$^{14}$—NH—R$^{15}$— in which R$^3$ to R$^{15}$ each independently represent a C$_3$ to C$_5$ alkylene group; and
NH—R$^1$ represents a guanidyl group.

2. The compound according to claim 1 or a pharmacologically acceptable salt thereof, wherein X represents a C$_4$ alkyl-SO$_2$-group.

3. A pharmaceutical composition comprising the compound according to claim 1, or a pharmacologically acceptable salt thereof.

4. An N-methyl-D-aspartate receptor activity inhibitor comprising a compound having the general formula (II) or a pharmacologically acceptable salt thereof:

X—NH—Y—NH—R$^1$  (II)

wherein
X represents an optionally substituted lower alkyl-SO$_2$-group;
Y represents a group selected from the group consisting of —R$^3$—NH—R$^4$—, —R$^5$—NH—R$^6$—NH—R$^7$—, —R$^8$—NH —R$^9$—NH—R$^{10}$—NH—R$^{11}$—, and —R$^{12}$—NH—R$^{13}$—NH—R$^{14}$—NH—R$^{15}$— in which R$^3$ to R$^{15}$ each independently represent a C$_3$ to C$_5$ alkylene group; and
NH—R$^1$ represents a guanidyl group.

5. A therapeutic drug for Alzheimer's disease or Parkinson's disease, comprising a compound having the general formula (II) or a pharmacologically acceptable salt thereof:

X—NH—Y—NH—R$^1$  (II)

wherein
X represents an optionally substituted lower alkyl-SO$_2$-group;
Y represents a group selected from the group consisting of —R$^3$—NH—R$^4$—, —R$^5$—NH—R$^6$—NH—R$^7$—, —R$^8$—NH—R$^9$—NH—R$^{10}$—NH—R$^{11}$—, and —R$^{12}$—NH—R$^{13}$—NH—R$^{14}$—NH—R$^{15}$— in which R$^3$ to R$^{15}$ each independently represent a C$_3$ to C$_5$ alkylene group; and
NH—R$^1$ represents a guanidyl group.

6. A pharmaceautical composition comprising the compound according to claim 2, or a pharmacologically acceptable salt thereof.

* * * * *